United States Patent
Claussen

(10) Patent No.: US 8,961,283 B2
(45) Date of Patent: Feb. 24, 2015

(54) AGRICULTURAL HARVESTING MACHINE

(71) Applicant: Frank Claussen, Greffen (DE)

(72) Inventor: Frank Claussen, Greffen (DE)

(73) Assignee: CLAAS Selbstfahrende Erntemaschinen GmbH, Harsewinkel (DE)

( * ) Notice: Subject to any disclaimer, the term of this patent is extended or adjusted under 35 U.S.C. 154(b) by 261 days.

(21) Appl. No.: 13/657,319

(22) Filed: Oct. 22, 2012

(65) Prior Publication Data

US 2014/0111792 A1    Apr. 24, 2014

(51) Int. Cl.
*A01D 75/18* (2006.01)
*A01F 12/16* (2006.01)
*G01N 21/55* (2014.01)

(52) U.S. Cl.
CPC ........................ *G01N 21/55* (2013.01)
USPC ................................................ 460/1; 460/7

(58) Field of Classification Search
USPC ........... 56/10.2 R, 10.2 A–10.2 E, 14.6, 13.5;
73/323–334, 431, 866.5, 865.9;
374/120, 121, 149; 460/1, 2, 7, 115, 3,
460/116, 119
See application file for complete search history.

(56) References Cited

U.S. PATENT DOCUMENTS

| | | | | |
|---|---|---|---|---|
| 5,704,200 | A * | 1/1998 | Chmielewski, Jr. et al. | ... 56/10.2 E |
| 6,100,526 | A * | 8/2000 | Mayes | 250/339.11 |
| 6,421,990 | B1 * | 7/2002 | Ohlemeyer et al. | 56/10.2 R |
| 7,478,518 | B2 * | 1/2009 | Kraus et al. | 56/10.2 R |
| 7,648,413 | B2 * | 1/2010 | Duquesne et al. | 460/112 |
| 8,073,599 | B2 * | 12/2011 | Goering et al. | 701/50 |
| 8,317,578 | B2 * | 11/2012 | Kormann et al. | 460/115 |
| 2005/0195406 | A1 | 9/2005 | Kormann et al. | |

FOREIGN PATENT DOCUMENTS

EP          1 570 723          9/2005

* cited by examiner

*Primary Examiner* — Robert Pezzuto
(74) *Attorney, Agent, or Firm* — Michael J. Striker

(57) ABSTRACT

An agricultural harvesting machine has a measurement device for investigating a crop flow conveyed through the harvesting machine. The measurement device includes at least one optical detection unit disposed at the crop flow for detecting light reflected by the crop and an evaluation unit for evaluating the spectrum of the detected light in order to derive properties of the crop. The evaluation unit is disposed at a position of the harvesting machine that is decoupled from mechanical loading by the crop flow to the greatest extent possible and is connected to the detection unit by way of at least one optical waveguide.

16 Claims, 2 Drawing Sheets

AGRICULTURAL HARVESTING MACHINE

CROSS-REFERENCE TO A RELATED APPLICATION

The invention described and claimed hereinbelow is also described in German Patent Application DE 10 2011 054841.6 filed on Oct. 27, 2011. This German Patent Application, subject matter of which is incorporated herein by reference, provides the basis for a claim of priority of invention under 35 U.S.C. 119(a)-(d).

BACKGROUND OF THE INVENTION

The invention relates broadly to an agricultural harvesting machine with a measurement device for investigating a crop flow that includes an optical detection unit for detecting light reflected by the crop and an evaluation unit that evaluates the spectrum of the detected light in order to derive properties of the crop (13) therefrom.

As is known, agricultural harvesting machines convey and process crop and, for many and various reasons, it is interesting to investigate crop conveyed through the machine during a harvesting operation with respect to the properties thereof, such as moisture and/or content of starch/sugar, proteins, crude fiber, oil, minerals, raw ash, etc.

A crop flow can be investigated in a manner known per se using a measurement device that operates on the basis of near infrared (NIR) spectroscopy. Measurement devices known from the prior art therefore comprise an optical detection unit disposed at the crop flow, which detects light reflected by the crop (which is irradiated with a light source). An evaluation unit signal-connected thereto and comprising a radiation detector analyzes the spectrum of the detected light in order to derive properties of the crop therefrom.

Measurement devices that operate in this manner, such as those available on the market for self-propelled forage harvesters, are designed as a compact assembly enclosed in a housing and are advantageously placed in the direct vicinity of the crop flow. For forage harvesters, the outer wall of the transfer device (also referred to as the "upper discharge chute") is typically used as the installation site for the housing of the measurement device. For example, EP 1 570 723 B1 describes a bracket system for a measurement device operating with near infrared spectroscopy, said bracket system being installable on the transfer device of a forage harvester.

The design described in EP 1 570 723 B1, however, has several disadvantages. For example, the sensors required for detection of the infrared light are exposed to strong vibrations and accelerations during operation, which are caused by crop flowing past and/or by operation-induced machine vibrations and accelerations that are transferred to the transfer device. During travel across uneven terrain in particular, vibrations have a particularly strong effect on the transfer device due to the lever effect (with increasing distance from the machine) and, in the extreme case, can be audibly perceived as impacts. The stability of the sensitive sensors is therefore limited. Also, considerable installation space is required to house the sensors, which can be provided on the outer wall of the transfer device only with the compromise of non-optimal positioning. Additionally, the design of the measurement device increases the risk of theft since the measurement device is attractive to thieves due to the high value and easy removability thereof.

SUMMARY OF THE INVENTION

The present invention overcomes the shortcomings of known arts, such as those mentioned above.

To that end, the present invention provides a harvesting machine of the initially mentioned type with a measurement device that displays a greater stability and improved placeability than those known in the conventional art. In addition, the arrangement of the measurement device in the invention is configured to be theft-proof.

In an embodiment, the present invention includes an evaluation unit of the measurement device that is disposed at a position of the harvesting machine that is decoupled from mechanical loading by the crop flow and/or other operation-induced accelerations to the greatest extent possible, and that is connected to the detection unit by way of at least one optical waveguide.

According to the invention it was recognized that main functional components of the measurement device, more particularly the optical detection unit and evaluation unit thereof, can be advantageously spatially separated from one another. According to the different design achieved as a result, only the optical detection unit is disposed in the vicinity of the crop flow, for the required incorporation in the harvesting process, and is therefore exposed to increased mechanical loading. The evaluation unit comprising the sensitive sensors for spectral analysis is disposed at a position of the harvesting machine that is spatially remote from the detection unit. Such positioning and design ensure reliable operation due to absence or limitation of mechanical influences.

By installing the evaluation unit in or at a driver's cab or a maintenance space of the harvesting machine, for example, positioning is provided that is mechanically decoupled to the greatest extent and advantageously ensures easy accessibility by an operator. For that matter, installing the evaluation unit in or at a driver's cab or a maintenance space of the harvesting machine ensures that the measurement device cannot be stolen in the closed state of the machine.

To ensure reliable evaluation of the detected light spectrum, according to the invention, the evaluation unit is connected to the detection unit by way of an optical waveguide. The advantage therefore results that only one optical detection of the crop is required in the vicinity of the crop flow, wherein the detected measurement signal (the light spectrum) is diverted largely interference-free by the optical waveguide into the safe surroundings of the evaluation unit. The aforementioned problem is therefore solved.

Advantageously, the detection unit is designed as a separate assembly that can be mounted at a crop-guiding component of the harvesting machine. All components of the detection unit are therefore combined to form one common installable assembly. The advantage results that the assembly can therefore be installed at different crop-guiding components and at different positions of the harvesting machine. The installation position can therefore also be changed subsequently. The detection unit can be removed rapidly for maintenance or repair.

In one form, the detection unit comprises an illumination source, which operates in the near infrared range and is used to illuminate the crop flowing past, and comprises an optical system for directing light reflected by the crop into the optical waveguide, wherein the optical waveguide directs the reflected light to a detector disposed in the evaluation unit. The reflected light is analyzed spectroscopically by way of the detector. It is also possible to provide a plurality of illumination sources in the detection unit for intensive illumination and/or for redundancy.

In order to position the detection unit exactly relative to the crop flow and to generate a measurement signal that is evaluated with good quality, means are preferably provided for adjusting the distance and/or orientation of the optical detection unit with respect to the crop flow to be investigated. The wear on components of the detection unit that come in contact with the crop, and the influence on the crop by components extending therein is therefore minimized. The detection unit could therefore be mounted on a component of the harvesting machine that guides crop (a material guide plate, for example) in such a way that the spacing and angle is adjusted by way of adjusting screws and/or spacer elements, for example.

To ensure reliable measurements over longer periods of time, at least one reference object used to calibrate the measurement device is assigned to the detection unit. Such a reference object comprises a white standard, for example, which is moved into the beam path for internal calibration of the evaluation unit. Light reflected by the reference object during calibration is directed by the detection unit and the optical waveguide onto the detector of the evaluation unit. A black reference is created, for example, by switching off the light source, which is switched on otherwise (during operation).

The optical waveguide is used primarily to transfer light from the detection unit to the evaluation unit and preferably comprises one or more glass fibers. Since the detection unit preferably also comprises an illumination source and/or a device for moving the reference object, the detection unit requires a power supply. In one form, the at least one optical waveguide is routed in a common cable together with electrical leads for power supply and/or actuation of the detection unit. The combination in a common cable provides the advantage of more compact and reliable handling of the conductor carriers during operation, more particularly when the detection unit is installed on a movable machine component (a transfer device, for example).

When the detection unit is installed on a movable machine component (a rotationally and height-adjustable transfer device, for example), a cable that accommodates the optical waveguide is enclosed at least in a section of a protective device that is subjected to particularly high mechanical loads. Such a protective device is used, inter alia, to prevent kinking and/or pinching of the optical waveguide, which is usually sensitive to kinking.

Due to the different design of the measurement device that is provided, i.e., the spatial separation of detection and evaluation unit, the measurement device may comprise a plurality of optical detection units, which are connected to a common evaluation unit by way of at least one optical waveguide each. One evaluation unit could therefore be used simultaneously (or in parallel operation) with a plurality of spatially differently disposed detection units. In such an embodiment, a signal splitter or a so-called multiplexer is necessary, possibly, for related common usage of the evaluation unit, in order to select the particular desired signal from a plurality of inputs that would then be present. The plurality of input units could be disposed one after the other and/or parallel to one another with respect to the crop flow. If the detection units are disposed one after the other, the crop could be investigated at different processing stages within the harvesting machine, for example. A parallel arrangement, with respect to the crop flow, is desirable for redundancy, for example, and/or to increase the reliability of the measurement results due to a higher investigated surface of the crop, as each detection unit optically detects one part of the crop flow.

Alternatively or in addition, a "non-on board" detection unit could be connectable to the evaluation unit, i.e., a detection unit that is stationary or entirely separate from the harvesting machine. In this manner, the evaluation unit located on-board the harvesting machine also could be used to investigate crop samples outside the harvesting machine. For the above-mentioned purposes it is advantageous to equip the evaluation unit with connections for a plurality of detection units.

The measurement device of the harvesting machine functions primarily according to the principle of infrared spectroscopy. The function of the measurement device could be expanded, however, by also assigning a camera to the detection unit for the optical detection of the crop and for generating images. The camera image captured in this manner could be output to a machine operator via a display thereby permitting the operator to perform an optical visual inspection in addition to the spectroscopic evaluation. Such operation renders it easier to detect contaminations of the optics, due to adhering crop, for example, which can easily result in corruption of the measurement results. The evaluation could take place in an automated manner by way of electronic image evaluation.

In an embodiment, the evaluation unit is equipped with a near infrared detector. The near infrared detector is, in turn, connected to an analysis and control device which is used to evaluate the spectra and to control the detection unit. The evaluation unit is preferably disposed in the driver's cab or in the maintenance space of the harvesting machine. When disposed in the driver's cab, easy access to the components by the driver and easy connection to periphery present in the driver's cab (for example, display and control elements and/or an existing machine control system) are realized. In addition, theft is made much more difficult. Furthermore, installation outside of the cab is feasible in that the evaluation unit can be attached to the driver's cab from the outside. Since the driver's cab is usually supported with respect to the rest of the machine in a vibration-damped manner, advantageous decoupling of the evaluation unit from operation-related vibrations is achieved without utilizing installation space in the driver's cab.

The invention is usable on different harvesting machines in which there is interest in investigating a crop flow. It can be a combine harvester, a cutting mechanism, a swather, impeller, self-loading forage wagon, a bale press, etc., for example, wherein crop is conveyed in each of the machines—in different manners—and investigation of the crop for the properties thereof plays a role.

The use on a self-propelled forage harvester is of high practical significance. When it is equipped with a transfer device in particular, an investigation of the crop exiting the machine can be advantageously achieved in that the detection unit is disposed at an outer wall of the transfer device in order to detect light reflected by the crop through a passage provided in the outer wall. By way of the different design provided according to the invention, the detection unit can be positioned in a region of the transfer device facing far away from the machine due to the design/weight, which are smaller/reduced compared to the prior art. The investigation therefore yields particularly good results since the crop can be detected more slowly and, therefore, optically more easily as the distance from the machine increases. Furthermore, since the curvature of the transfer device decreases as the distance from the machine increases, the friction forces of the crop at the outer wall become less, and therefore the optics, which are required for detection, undergo less wear and contamination by the crop.

The invention is advantageous with respect to maintenance and repair, particularly for use on a forage harvester, as the evaluation unit can be switched from an operating state in which it is attached to the driver's cab, into a maintenance state in which it is attached to the transfer device, while retaining the connection to the detection unit. In this configuration, the evaluation unit is therefore connected to the detection unit via the optical waveguide in both an operating state and in a maintenance state attached to the transfer device.

If the transfer device must be removed from the rest of the machine, for example, for maintenance, repair or assembly, or reinstalled thereon, this can take place in the maintenance state, wherein the detection unit, including the optical waveguide, installed on the transfer device and the evaluation unit temporarily attached thereto can remain connected. This means that the optical waveguide connection between the detection and evaluation unit does not need to be separated during deinstallation of the transfer device. After the transfer device is installed on the machine, the evaluation unit can be brought into the operating state thereof once more, i.e. it can be attached to the driver's cab, without having to restore the optical waveguide connection.

BRIEF DESCRIPTION OF THE DRAWINGS

Further features and advantages of the invention will become apparent from the description of embodiments that follows, with reference to the attached figures, wherein.

DETAILED DESCRIPTION OF THE PREFERRED EMBODIMENTS

The following is a detailed description of example embodiments of the invention depicted in the accompanying drawings. The example embodiments are presented in such detail as to clearly communicate the invention and are designed to make such embodiments obvious to a person of ordinary skill in the art. However, the amount of detail offered is not intended to limit the anticipated variations of embodiments; on the contrary, the intention is to cover all modifications, equivalents, and alternatives falling within the spirit and scope of the present invention, as defined by the appended claims.

Figure 1:
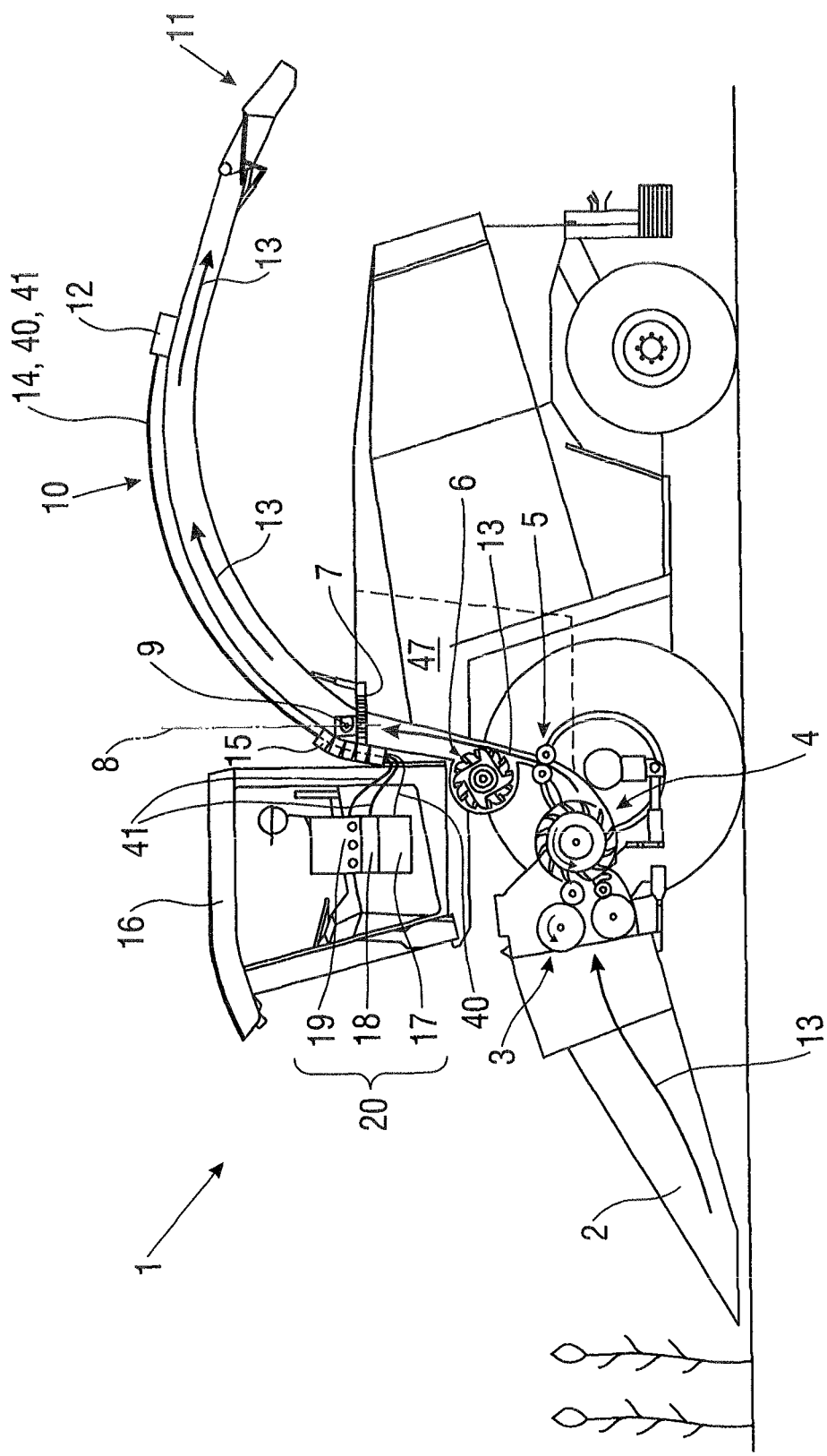
FIG. 1 a schematic side view of a self-propelled forage harvester according to the invention.

FIG. 1 shows a schematic side view of a harvesting machine according to the invention, which is a self-propelled forage harvester 1. The forage harvester 1 is equipped with front and rear wheels for harvesting travel over a field and is driven by an engine unit. During harvesting operation, the forage harvester 1 cuts the plant crop (shown at the left in the image) from the field using a front harvesting attachment 2. The cut crop is fed in the form of a crop flow 13, indicated by arrows along the conveyance direction of the crop 13, to downstream working and conveyance devices of the forage harvester 1, for subsequent ejection into a transport container (not shown).

From the front harvesting attachment 2, the crop 13 first reaches an intake assembly 3, from which the crop is fed, after precompression by pairs of intake rollers, to a chopping assembly 4. Via interaction of a rotating chopper drum equipped with knives and a stationary shear bar, the crop is fragmentized (chopped). The fragmentized crop travels through a conveyor chute, which rises from underneath a driver's cab 16, through a conditioning device 5 and a post-accelerator 6 into a transfer device 10. The transfer device has a curved shape and ejects the crop 13 by way of a discharge flap 11 and is therefore also referred to as an upper discharge chute. The transfer device 10 can be rotated by way of a driven flange joint 7 about a vertical axis 8 with respect to the machine frame of the forage harvester 1 and can be swiveled vertically about a horizontal rotational axis 9 by way of a lifting cylinder.

The forage harvester 1 is equipped with a measurement device for investigation of the crop 13 with respect to the properties thereof such as moisture and/or content of starch/sugar, proteins, crude fiber, oil, minerals, raw ash, etc. The measurement device mainly comprises an optical detection unit 12, which is mounted in the direct vicinity of the crop flow 13 on an outer wall of the transfer device 10, and an evaluation unit 20. The evaluation unit 20 is decoupled from the mechanical load by the crop flow and is disposed in the driver's cab 16. The evaluation unit 20 is connected to the detection unit 12 by way of an optical waveguide 40 routed in a cable 14. The detection unit 12 is designed as a closed assembly integrated in a housing and can therefore be easily installed on and removed from the transfer device 10. As shown in FIG. 1, the detection unit 12 is disposed at a position of the transfer device 10 that is closer to the discharge flap 11 facing away from the machine than the shoulder of the transfer device 10 on the flange joint 7. The curvature of the transfer device 10 in this region is negligible.

Figure 2:
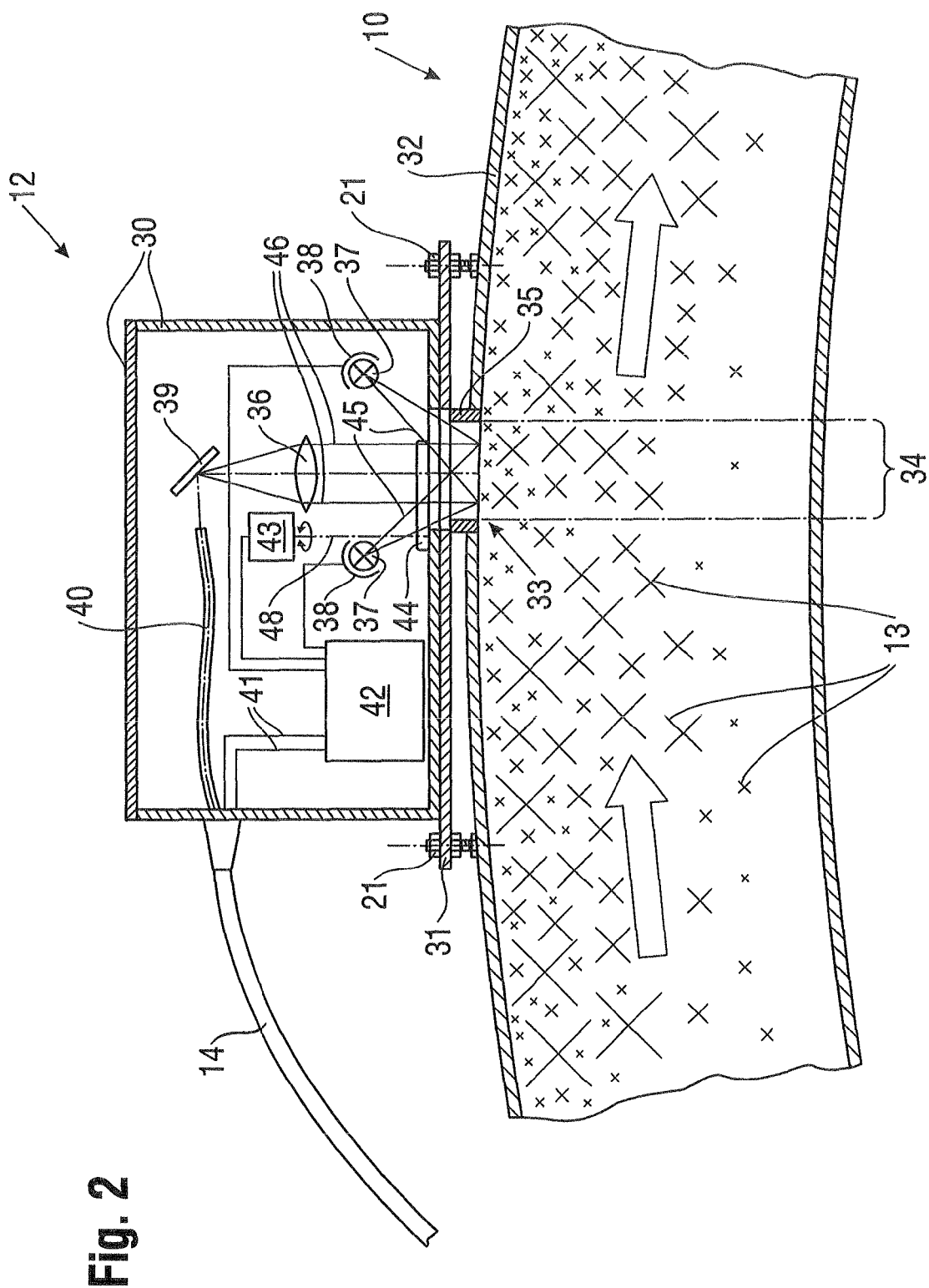
FIG. 2 a schematic detailed view of a detection unit installed on the forage harvester according to FIG. 1, in a sectional view.

FIG. 2 provides a schematic detailed side view of the detection unit 12 mounted on the transfer device 10. An exposed section of the transfer device 10 also is shown in FIG. 2. A passage 33 is formed at an outer wall 32 of the transfer device 10. Crop 13 conveyed through the transfer device 10 is conveyed directly past said passage 33 as indicated by the arrow direction.

The detection unit 12 is disposed at the passage 33 in a suitable manner in order to detect light reflected by the crop 13. To this end, the detection unit 12 comprises a housing 30, which is fastened to a base plate 31. The base plate 31 is retained by way of an adjusting device 21 against the outer wall 32 of the transfer device 10, thereby enabling the entire detection unit 12 to be adjusted with respect to the distance from and orientation relative to the transfer device 10. This makes it possible to perform an exact adjustment, which is required for the measurement, of a reflectance region 34 formed on the surface of the crop flow 13.

The housing 30 of the detection unit 12 accommodates optics, which substantially comprise a tube 35, a lens 36, a redirection device 39 and two light sources 37 (preferably infrared light sources) with an associated reflector 38. By way of the adjustment device 21 the distance position of the detection unit 12 relative to the outer wall 32 can be adjusted such that the tube 35 only minimally disrupts the crop 13 flowing past and is therefore subject to minimal wear.

The light sources 37 are disposed with mirror symmetry relative to rays entering the lens 36 in the center and are oriented such that a reflectance region 34 on the surface of the crop flow 13 located directly underneath the tube 35 is irradiated with infrared light 45 at an approximate angle of 45° in each case.

Light 46 reflected by the crop 13 in the reflectance region 34 is bundled by the lens 36, is deflected in a redirection device 39 (mirror or prism) and enters an optical waveguide 40. The redirection device 39 reduces the installation height of the housing 30 in that the reflected light 46 enters the optical waveguide 40 in a direction that is parallel to the detachable rear wall of the housing 30.

A control device (with voltage supply) 42 also is accommodated in the housing 30. The two light sources 37 are first thereby supplied with current. In addition, a servomotor 43 is thereby actuated. The servomotor 43 swivels a reference object 44 into and out of the beam path of the optics, as needed, in order to calibrate the measurement device. To this end, the reference object can be rotated about an adjustment axis 48 of the motor 43 and comprises a white or black standard, for example. Any other design of a drive for moving the reference object 44 into and out of the beam path is feasible. For example, the installation space of the housing 30 could be further reduced by way of a bevel gear provided between the servomotor 43 and the reference object 44. Alternatively, a reference object could be disposed such that it lies in the detected beam path permanently without the need for mechanical motion.

During calibration of the measurement device, the reference object 44 is irradiated with infrared light 45 instead of or in addition to the crop 13. For example, a known radiation spectrum is reflected by the white standard and is directed through the lens 36, the redirection device 39 and the optical waveguide 40 to the evaluation unit 20, in order to perform calibration.

The control device (with voltage supply) 42 is connected to the evaluation unit 20 by way of electrical leads 41 in order to be supplied with voltage and to have signal contact with the evaluation unit 20, e.g., in order to perform calibration.

The optical waveguide 40 and the electrical lead 41 are accommodated outside of the housing 30 in a common cable 14. The cable 14 can be removed from the housing 30 and plugged therein using a suitable coupling (not shown), thereby enabling the detection unit 12 to be installed on and removed from the transfer device 10 with the cable 14 installed.

As shown in FIG. 1, the cable 14, including the integrated optical waveguide 40 and the electrical lead 41, extends from the detection unit 12 along the transfer device 10 first to the shoulder of the transfer device 10 in the region of the flange joint 7. To permit rotational and vertical motions of the transfer device 10 about the vertical axis 8 and the horizontal axis 9, respectively, the cable 14 has adequate play in this region and is preferably enclosed by a flexible protective device 15. Flexible protective device 15 protects the cable 14 against kinking, pinching and/or tensile stress in this region while ensuring the mobility of the transfer device 10.

The cable 14 further extends through a passage in the rear wall of the driver's cab 16 to the evaluation unit 20 disposed there. Alternatively, the evaluation unit 20 can be disposed at least partially in a maintenance space 47, which is indicated by dashed lines, behind the post-accelerator 6 or the conditioning device 5.

As shown, the evaluation unit 20 comprises a detector 17 for infrared light, an analysis and control device 18 and an operating and display device 19. The detector 17 receives the light spectrum transmitted by the detection unit 12 by way of the optical waveguide 40 and detects the spectral components thereof. The analysis and control device 18 is connected to the detector 17 and determines the moisture and/or the content of certain ingredients (starch/sugar, proteins, crude fiber, oil, minerals, raw ash, etc.) in the crop 13, inter alia, by comparison with reference data.

An operating and display device 19 connected to the analysis and control device 18 also is disposed in the driver's cab 16 and is used as a user interface for a machine operator. Current measured values for individual ingredients or other measurement information, for example, are displayed on an assigned display. All types of adjustments can be made using operating devices; calibration, in particular, can be initiated manually.

The harvesting machine described above has the advantage that the measurement device thereof is less susceptible to interference because of the accommodation of the evaluation unit 20 in a manner that is decoupled from vibrations and motion. The detection unit 12 preferably embodies a light weight and compact design, thereby permitting placement close to the end of the transfer device 10 facing away from the machine, which is advantageous for the quality of the measurement. Since the evaluation unit 20 (which is valuable with respect to the individual components thereof) is disposed at a secure location in the driver's cab 16 or in a maintenance space 47, theft is made much more difficult.

It is within the scope of the invention that a plurality of detection units can be disposed at different points of the crop conveyed through the machine and work together with a common evaluation unit. Connection of a "non-on board" detection unit to the evaluation unit is also possible, in order to investigate crop samples in a stationary manner, for example. Due to the use of the evaluation unit on board the harvesting machine, a detection unit to be used can be advantageously designed relatively small and lightweight, thereby making it easy to handle.

The following list of reference signs of various elements mentioned above is included (as follows), for ease of explanation:

REFERENCE NUMERALS 1 forage harvester
2 front harvesting attachment
3 intake assembly
4 chopping assembly
5 conditioning device
6 post-accelerator
7 flange joint
8 vertical axis of rotation
9 horizontal axis of rotation
10 transfer device
11 discharge flap
12 detection unit
13 crop/crop flow
14 cable
15 protective device
16 driver's cab
17 detector
18 analysis and control unit
19 operating and display device
20 evaluation unit
21 adjustment device
30 housing
31 base plate
32 outer wall
33 passage
34 reflectance region
35 tube
36 lens
37 light source
38 reflector
39 redirection device
40 optical waveguide
41 electrical lead
42 control device/voltage supply
43 servomotor
44 reference object
45 light beam
46 reflected light beam
47 maintenance space
48 adjustment axis As will be evident to persons skilled in the art, the foregoing detailed description and figures are presented as examples of the invention, and that variations are contemplated that do not depart from the fair scope of the teachings and descriptions set forth in this disclosure. The foregoing is not intended to limit what has been invented, except to the extent that the following claims so limit that.

What is claimed is:

1. An agricultural harvesting machine (1) includes a measurement device for investigating a crop flow (13) conveyed through the harvesting machine (1), wherein the measurement device comprises:
   at least one optical detection unit (12) disposed at the crop flow (13), which detects light (46) reflected by the crop (13), and
   an evaluation unit (20), which evaluates the spectrum of the detected light (46) in order to derive properties of the crop (13) therefrom,
   wherein the evaluation unit (20) is disposed at a position of the harvesting machine (13) that is substantially decoupled from mechanical loading by the crop flow (13), decoupled from other operation-induced acceleration or both, and is connected to the detection unit (12) by way of at least one optical waveguide (40).

2. The harvesting machine according to claim 1, wherein the detection unit (12) comprises a separate assembly that is installed at a crop-guiding component (10) of the harvesting machine (1).

3. The harvesting machine according to claim 1, wherein the detection unit (12) comprises an illumination source (37) and optics (35, 36, 39) for directing light (46) reflected by the crop (13) into the optical waveguide (40), and wherein the optical waveguide (40) directs the reflected light (46) to a detector (17) disposed in the evaluation unit (20).

4. The harvesting machine according to claim 1, wherein means (21) are provided for adjusting the distance for adjusting the orientation of the optical detection unit (12) with respect to the crop flow (13) to be investigated or both.

5. The harvesting machine according to claim 1, wherein at least one reference object (44) used to calibrate the measurement device is assigned to the detection unit (12).

6. The harvesting machine according to claim 1, wherein the at least one optical waveguide (40) is routed together with electrical leads (41) for power supply, for actuation of the detection unit (12) or both, in a common cable (14).

7. The harvesting machine according to claim 1, wherein a cable (14) accommodating the optical waveguide (40) is enclosed at least in a section of a protective device (15) in order to withstand particularly high mechanical loads.

8. The harvesting machine according to claim 1, wherein the measurement device comprises a plurality of optical detection units (12), each of which is connected by way of at least one optical waveguide (40) to a common evaluation unit (20), and wherein the detection units (12) are disposed one behind the other, parallel to one another or both, with respect to the crop flow (13).

9. The harvesting machine according to claim 1, wherein a camera for the optical detection of the crop and for generating images also is assigned to the detection unit (12).

10. The harvesting machine according to claim 1, wherein the evaluation unit (20) is disposed in a driver's cab (16) of the harvesting machine (1) provided for control of the harvesting machine (1) by an operator.

11. The harvesting machine according to claim 1, wherein the evaluation unit (20) is located outside the driver's cab (16) and can be attached to the driver's cab (16) from the outside.

12. The harvesting machine according to claim 1, wherein the evaluation unit (20) is disposed in a maintenance space (47) of the harvesting machine (1).

13. The harvesting machine according claim 1, wherein the harvesting machine is a forage harvester (1) comprising a transfer device (10).

14. The harvesting machine according to claim 1, wherein the evaluation unit (20) is switched from an operating state in which the evaluation unit is attached to the driver's cab (16), into a maintenance state in which the evaluation unit is attached to the transfer device (10) while retaining the connection to the detection unit (12).

15. The harvesting machine according to claim 14, wherein the detection unit (12) is disposed at an outer wall (32) of the transfer device (10) in order to detect light (46) reflected by the crop (13) through a passage (33) provided in the outer wall (32).

16. The harvesting machine according to claim 1, wherein the harvesting machine is a combine harvester, a swather, an impeller, a cutting mechanism, a self-loading forage wagon or a bale press.

* * * * *

UNITED STATES PATENT AND TRADEMARK OFFICE
CERTIFICATE OF CORRECTION

| | | |
|---|---|---|
| PATENT NO. | : 8,961,283 B2 | Page 1 of 1 |
| APPLICATION NO. | : 13/657319 | |
| DATED | : February 24, 2015 | |
| INVENTOR(S) | : Claussen | |

It is certified that error appears in the above-identified patent and that said Letters Patent is hereby corrected as shown below:

Title Page, insert item --(30) Application Priority Data
2011 054 841.6..........[DE]....................Oct. 27, 2011--

Signed and Sealed this
Seventh Day of July, 2015

Michelle K. Lee
*Director of the United States Patent and Trademark Office*